(12) United States Patent
Lutovsky et al.

(10) Patent No.: US 11,559,499 B1
(45) Date of Patent: Jan. 24, 2023

(54) LOTION AND TINCTURES CONTAINING CBD OIL INCLUDING PREPARATION AND USE THEREOF

(71) Applicants: Greg Lutovsky, Cle Elum, WA (US); Alexa Blanken, Cle Elum, WA (US)

(72) Inventors: Greg Lutovsky, Cle Elum, WA (US); Alexa Blanken, Cle Elum, WA (US)

(*) Notice: Subject to any disclaimer, the term of this patent is extended or adjusted under 35 U.S.C. 154(b) by 0 days.

(21) Appl. No.: 17/382,306

(22) Filed: Jul. 21, 2021

Related U.S. Application Data

(60) Provisional application No. 63/054,785, filed on Jul. 21, 2020.

(51) Int. Cl.
| | |
|---|---|
| A61K 31/05 | (2006.01) |
| A61K 31/352 | (2006.01) |
| A61K 36/888 | (2006.01) |
| A61K 35/644 | (2015.01) |
| A61K 36/736 | (2006.01) |
| A61K 47/44 | (2017.01) |
| A61K 36/28 | (2006.01) |
| A61K 36/185 | (2006.01) |

(52) U.S. Cl.
CPC .......... *A61K 31/05* (2013.01); *A61K 31/352* (2013.01); *A61K 35/644* (2013.01); *A61K 36/185* (2013.01); *A61K 36/28* (2013.01); *A61K 36/736* (2013.01); *A61K 36/888* (2013.01); *A61K 47/44* (2013.01)

(58) Field of Classification Search
None
See application file for complete search history.

(56) References Cited

FOREIGN PATENT DOCUMENTS

CN          108685728 A   * 10/2018

* cited by examiner

*Primary Examiner* — Michael V Meller
(74) *Attorney, Agent, or Firm* — Alig Patent Law; Graham Casanova Alig

(57) ABSTRACT

Here is presented a novel formulation of a topical treatment containing cannabidiol (CBD), as well as shea butter, cocoa butter coconut oil, aloe vera, body butter, lavender, lemongrass and tangerine. Such formulation may be applied to the skin in a variety of applications. The formulations are made with nearly no THC. Formulations include massage oil, pain relief cream, gardener's relief cream, warming cream, hand and body lotion grip, massage lotion glide and a gardener's relief oil.

1 Claim, No Drawings

LOTION AND TINCTURES CONTAINING CBD OIL INCLUDING PREPARATION AND USE THEREOF

FIELD OF THE DISCLOSURE

Here is presented a novel formulation of a topical treatment containing cannabidiol (CBD), as well as shea butter, cocoa butter coconut oil, aloe vera, body butter, lavender, lemongrass and tangerine. Such formulation may be applied to the skin in a variety of applications.

BACKGROUND

Cannabidiol is the main non-psychotropic phytocannabinoid present in the *Cannabis sativa* plant, constituting up to 40 percent of its extract. CBD is a safe compound with a wide range of therapeutic applications, including the treatment of psychiatric disorders.

While CBD oil has been used in other topical treatments, for instance, U.S. Pat. No. 11,040,017, entitled "Cannabidiol formulation" to Elizabeth Merritt, hereby incorporated by reference in its entirety. One of the undesirable characteristics of these cannabidiol formulations is that they contain a significant presence of THC. While this patent mitigates the euphoric effect of THC, the mere presence of THC is undesirable to some consumers. In particular, a presence of greater than 0.3 percent by weight classifies the substance as a 'controlled substance; according to current US law. It would be desirable to have a therapeutic lotion containing CBD oil that has no—or a nominal amount—of THC so that it can be sold, distributed and used in the US without a specific license.

Without the presence of THC, CBD is a safe compound with a wide range of therapeutic applications, including the treatment of psychiatric disorders These findings make this substance an attractive candidate for therapeutic use. However, such use has some limiting factors. In addition to its low and variable oral bioavailability in humans, pure cannabidiol possesses a narrow therapeutic dose range. It would be desirable to have a wider therapeutic dose range and a more bioavailable form of cannabidiol. Here are presented mixtures, lotions, creams and tinctures that have adjuvants and additives that widen the therapeutic dose range as well as make CBD oil more bioavailable to humans when used topically while having little or no THC present to avoid the complications of that substance.

SUMMARY OF THE INVENTION

Here is presented an over-the-counter CBD containing massage lotion comprising: at least 60% sweet almond oil by volume; at least 0.5% CBD oil by volume; and at least 5% hemp seed oil by volume. Wherein any ingredient of the cream contains either no TCH or TCH at a concentration of below about 0.3% by weight. Preferably, the massage lotion contains between about 0.7 and 1.2% CDB oil by volume. More preferably, the massage lotion contains about 1% CDB oil by volume.

A more preferred embodiment of the invention is a massage lotion which contains between about 5% and 10% hemp oil by volume. A most preferred embodiment of the invention is a massage lotion that contains about 8% hemp oil by volume.

Another embodiment of the invention is an over-the-counter CBD containing pain relief cream comprising at least 15% body butter by volume; at least 5% white bees wax by volume; at least 7% shea butter by volume; at least 5% coconut oil by volume; at least 4% *arnica* butter by volume; at least 1.0% CBD oil by volume. After preparation, the cream has been whipped to incorporate at least 10% gas by volume. More preferably the cream has been whipped to incorporate at least 25% gas by volume. Most preferably the cream has been whipped to incorporate at least 50% gas by volume. Wherein any ingredient of the cream contains either no TCH or TCH at a concentration of below about 0.3% by weight. Preferably, the cream was heated to at least 85° C. for at least ten minutes. Preferably, the cream contains between about 25% and about 30% body butter by volume. More preferably, the cream contains between about 1.5 and about 2.5% CBD oil by volume. Most preferably, the cream contains about 2.0 CBD oil by volume.

Another embodiment of the invention is an over-the-counter CBD containing lotions comprising at least 70% lotion base by volume; at least 1% *Arnica* butter by volume; at least 5% *Arnica* oil by volume; and at least 0.5% CBD oil by volume. Wherein any ingredient of the cream contains either no TCH or TCH at a concentration of below about 0.3% by weight. Preferably, the lotion contains less than about 1.0% CBD oil by volume. More preferably, the lotion contains between about 0.7 and 0.9% CBD oil by volume.

DETAILED DESCRIPTION OF THE INVENTION

Definitions

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments.

As used here, the term "ounce", abbreviated "oz." generally refers to fluid measure. The term ounce is used throughout the disclosure and is intended to mean the English unit of measure for mass, equal to about 29.5735 ml.

As used here, the term "Fahrenheit" or "degree F." or "F" are used interchangeably and mean the English unit of temperature, Fahrenheit. The temperature of 32 degrees F. is exactly equal to 0 degrees Celsius and one unit of Celsius is approximately 1.8 units of Fahrenheit.

As used here, the terms "THCA" and "Tetrahydrocannabinolic acid" are used interchangeably. Both terms as used herein are meant to refer to the chemical tetrahydrocannabinolic acid. Tetrahydrocannabinolic acid is a precursor of tetrahydrocannabinol (THC), an active component of *cannabis*. In other literature THCA is also referred to as THCA, 2-COOH-THC; conjugate base tetrahydrocannabinolate these terms are considered synonymous with TCHA for the purpose of this disclosure.

The terms "THC" and "Tetrahydrocannabinol" are used interchangeably herein. Both terms refer to the chemical compound tetrahydrocannabinol and its cannabinoid isomers. Tetrahydrocannabinol along with its double bond isomers and their stereoisomers are commonly found in *cannabis*. THC (including THC isomers) is the principal psychoactive constituent of *cannabis*. Particularly, dronabinol, a pharmaceutical form of THC is included as a chemical compound referred to herein as THC.

As used herein the terms "CBD", "CBD oil" and "Cannabidiol" (CBD) are terms used interchangeably herein. Each of these terms refers to the chemical compound "cannabidiol" and is a phytocannabinoid commonly found in *cannabis* plants. For the purpose of this invention CBD as used herein means the CBD as added to the mixtures, lotions, cosmetics and tinctures herein contains no more than 0.3 percent THC on a dry weight basis.

The term "*Cannabis*" as used herein collectively refers to any one or combination of the plant *Cannabis sativa, Cannabis indica, Cannabis ruderalis*. Specific reference to a species of *cannabis* refers specifically to that species. Specific reference to a strain and/or cultivar of a *cannabis* species specifically refers to the named strain and/or cultivar. *Cannabis* is also known as "marijuana". There are other terms for *cannabis* that are used in the art and society that are known to refer to the *cannabis* plant, its flower and or the active compounds of *cannabis*. Those terms are too numerous and fluid to recite here but are recognized by those of skill in the art.

DESCRIPTION OF THE INVENTION

The present disclosure presents lotions and tinctures containing CBD oil. Each embodiment of the invention is designed to enhance the various beneficial uses of CBD oil.

Cannabidiol

Cannabidiol (commonly referred to as "CBD" and "CDB oil" all terms are used interchangeably herein) is a major phytocannabinoid present in the *Cannabis sativa* plant. It lacks the psychotomimetic and other psychotropic effects that the main plant compound tetrahydrocannabinol (THC). Cannabidiol while lacking these effects is also shown to antagonize THC. It is now well established, that CBD has a therapeutic potential over a wide range of non-psychiatric and psychiatric disorders such as anxiety, depression and psychosis.

In vivo studies indicate that these benefits while unitary depend on the behavioral response of the patient and the effect measured. While not wishing to be bound by theory, acute anxiolytic and antidepressant-like effects seem to rely mainly on facilitation of 5-HT1A-mediated neurotransmission in key brain areas related to defensive responses, including the dorsal periaqueductal grey, bed nucleus of the stria terminalis and medial prefrontal cortex. Other effects, such as anti-compulsive, increased extinction and impaired reconsolidation of aversive memories, and facilitation of adult hippocampal neurogenesis could depend on potentiation of anandamide-mediated neurotransmission. Finally, activation of TRPV1 channels may help to explain the antipsychotic effect and the bell-shaped dose-response curves commonly observed with cannabidiol. Various studies indicate other possible neuroactive mechanisms including inhibition of adenosine uptake, inverse agonism at CB2 receptor, CB1 receptor antagonism, GPR55 antagonism, PPARg receptors agonism, intracellular ($Ca2\flat$) increase, etc.). Given, its safety profile and a wide range of therapeutic potential, cannabidiol has great potential to alieve many human anxieties.

Cannabidiol is the main non-psychotropic phytocannabinoid present in the *Cannabis sativa* plant, constituting up to 40 percent of its extract. CBD is a safe compound with a wide range of therapeutic applications, including the treatment of psychiatric disorders. These findings make this substance an attractive candidate for therapeutic use. However, such use has some limiting factors. In addition to its low and variable oral bioavailability in humans, pure cannabidiol possesses a narrow therapeutic dose range. It would be desirable to have a wider therapeutic dose range and a more bioavailable form of cannabidiol. Such a formulation is presently presented being topical formulations containing cannabidiol and a cultivated blend of carriers and adjuvants to transdermally deliver active cannabidiol in a therapeutic dose.

THC and THCA are two forms of the psychoactive component of *cannabis*. Neither chemical is used as an additive in the present invention. All ingredients used herein that are derived from a *cannabis* plant are selected to contain little to no THC and/or THCA, less than 0.3% by weight.

Other Ingredients

Shea Butter

Shea butter is a fat extracted from the nuts of the shea tree, *Vitellaria paradoxa*. The shea tree is endemic to tropical Africa. The fat is solid at warm temperatures and has an off-white or ivory color. The shea butter comes from two oily kernels within the shea tree seed. Typically during processing, the kernel is removed from the seed. The seed is ground into a powder and boiled in water. The butter then rises to the top of the water and becomes solid.

Shea butter extract is a complex fat that generally contains the following fatty acids: oleic acid (40-60%), stearic acid (20-50%), linoleic acid (3-11%), palmitic acid (2-9%), linolenic acid (<1%) and arachidic acid (<1%).

Topically, shea butter is believed to work as an emollient. Used alone, shea butter generally softens and/or smooths dry skin. Shea butter also contains substances that can reduce skin swelling. Shea butter is often used to treat eczema.

Cocoa Butter

Cocoa Butter is derived from cocoa beans. To harness cocoa butter, the beans are taken out of the larger cacao plant. Then they're roasted, stripped, and pressed to separate out the fat—the cocoa butter. Cocoa butter is distinct from cocoa powder which is processed from the remnants of cocoa butter production.

Cocoa butter (cacao fat) naturally occurs in the cocoa bean at about 50% of the cocoa nib. Cocoa butter is resistant to oxidation due to high levels of natural tocopherols and fatty acid composition. Cocoa butter contains a high proportion of saturated fats as well as monounsaturated oleic acid, which typically occurs in each triglyceride. A typical fatty acid profile is shown below:

| | | |
|---|---|---|
| Stearic | (C18:0) | 34.5% |
| Oleic | (C18:1) | 34.5% |
| Palmitic | (C16:0) | 26.0% |
| Linoleic | (C18:2) | 3.2% |
| Arachidic | (C20:0) | 1.0% |
| Palmitoleic | (C16:1) | 0.3% |
| Other Fatty Acids | | 0.5% |

Additionally, cocoa butter contains natural antioxidant Vitamin E, as well as a number of other vitamins and minerals. Cocoa butter's melting point is just below human body temperature. Because of this physical property, it is often used as an adjuvant in pharmaceutical compositions.

Coconut Oil

Coconut oil is made up of a mixture of saturated, monounsaturated and polyunsaturated fats. While it is high in saturated fat, coconut oil also contains heart-healthy polyunsaturated and monounsaturated fats that are important for brain function and overall growth and development.

Coconut oil is classified as either refined and unrefined types based on differences in coconut oil extraction. Refined coconut oil is extracted from coconuts that are baked first. The oil is then bleached to remove impurities. Some refined coconut oils contain partially hydrogenated fats, which are associated with cardiovascular disease. Unrefined coconut oil, also called "virgin" coconut oil, is extracted from fresh coconuts. This process maintains more of the anti-inflammatory and antioxidant benefits of the oil.

Coconut oil is 99% fat by content. The vast majority of this fat (90-95%) is saturated fat. The saturated fat in coconut oil is made up of seven different types of fatty acids, including caproic, caprylic, capric, lauric, myristic, palmitic, and stearic acid. Of the seven types of acid, lauric acid is the most predominant. The monounsaturated fat in coconut oil is made entirely of oleic acid. A smaller portion is polyunsaturated fat, all of this fat is Linoleic acid. Linoleic acid is considered to be an essential fatty acid.

Plant sterols have a chemical structure that mimics blood cholesterol and may help to block the absorption of cholesterol in the body. Epidemiological studies find that groups of people who include coconut as part of their native diets (e.g., India, Philippines, Polynesia) have low rates of cardiovascular disease.

Hemp Seed Oil

Hemp is a plant, *Cannabis sativa*. It is a species of *cannabis*. But unlike other varieties of *cannabis*, hemp contains very low levels of tetrahydrocannabinol (THC), less than 0.3% by weight. Hemp is used commercially for hemp products in the U.S. and worldwide, as food and/or medicine such as hemp flowers, leaves, seed, seed oil, and protein.

Hemp seed oil, synonymous with "hemp oil", is made from the *cannabis* plant, Hemp. The oil contains little to no tetrahydrocannabinol (THC), less than 0.3% by weight. Hemp contains a portion of cannabidiol (CBD), described above.

Hemp oil has been used as a remedy for a range of conditions including skin issues and stress. Hemp oil may also reduce inflammation in the body.

In addition to CBD, Hemp oil contains large amounts of omega-6 and omega-3 fats, which are two types of unsaturated fat s, or "good fats," and all nine essential amino acids, the materials your body uses to make protein.

The hemp seed oil used in the present invention contains little to no tetrahydrocannabinol (THC), less than 0.3% by weight As used in a massage lotion, hemp oil is preferably used at a concentration of between about 1 and about 15% by volume, more preferably hemp seed oil at a concentration of between about 3 and about 12% by volume, still, more preferably hemp seed oil is used at a concentration of between about 5 and about 10% by volume, most preferably hemp seed oil is used at a concentration of about 8% by volume.

Almond Oil

Almond oil, derived from the species Oleum amygdalae, has long been used in complementary medicine circles for its numerous health benefits. Almonds and almond oil are reported to have many beneficial properties including anti-inflammatory, immunity-boosting and anti-hepatotoxicity effects. Further, associations between almond oil and improved bowel transit have been made, which consequently reduces irritable bowel syndrome symptoms. Moreover, cardiovascular benefits have also been identified with almond oil elevating the levels of so-called 'good cholesterol', high-density lipoproteins (HDL), whilst it reduces low-density lipoproteins (LDL). Historically, almond oil had been used in Ancient Chinese, Ayurvedic and Greco-Persian schools of Medicine to treat dry skin conditions such as psoriasis and eczema. Further, it is through anecdotal evidence and clinical experiences that almond oil seemingly reduces hypertrophic scarring post-operatively, smoothes and rejuvenates skin. Almond oil has emollient and sclerosant properties and, therefore, has been used to improve complexion and skin tone.

Sweet Almond Oil

Sweet almond oil is a specific state of almond oil. Sweet almond oil generally contains the following nutrients: Vitamin A, Vitamin E, fatty acids (including essential fatty acids: oleic, linoleic, palmitic, and stearic acids), and zinc. Sweet almond oil is a non-volatile oil (as referred to as a "fixed oil"). This is distinguished from bitter almond oil which is volatile (commonly noted as an essential oil).

As used in some embodiments of the present invention, Sweet Almond oil comprises between about 50 and about 90% of the mixture by volume, preferably sweet almond oil comprises between about 60 and about 80% of the mixture by volume, more preferably sweet almond oil comprises between about 70 and about 75% of the mixture by volume, most preferably sweet almond oil comprises about 73% of the mixture by volume.

Aloe Vera Liquid

Although there are at least 420 different plant species of Aloe. Aloe vera, as used herein, specifically refers to the Aloe vera plant, which is the most common form used in Aloe-based products. Aloe vera liquid is shown to provide excellent emollient and moisturizing properties to the skin. It is also known to be soothing and healing for sunburned skin.

Aloe vera liquid is prepared through the following typical process:

Organically grown leaves are harvested, washed and filleted.

The filleted leaves are then rinsed to remove aloin which is a bitter, yellow-brown compound naturally found in aloe vera. Aloin is known to cause purgative side-effects when ingested.

After removal of the aloin, the leaves are run through a grinder and then the pulp and fiber are removed without the use of enzymes.

The liquid is then heat-treated, run through a carbon filter and then concentrated.

Once concentrated, preservatives are added, and the pH is adjusted by adding citric acid. The concentrate is filtered again. Q.v. with deionized water. The reconstituted liquid is filtered a final time before use.

Body Butter

Body butter is a thick heavy cream used in pharmaceuticals and cosmetics. Typically Body butter contains purified water, mineral oil, isopropyl myristate, cetyl alcohol, glycerol monosterate, stearic acid, glycerine, propylene glycol, cetereth-20, carbomer, aloe vera, disodium EDTA, dimethicone, petrolatum, methylparaben triethanolamine, propylene glycol, diazolidinyl urea, iodopropynyl butylcarbamate, propylparaben, and beeswax.

For consistency, it is crucial that after body butter is mixed with other components that it is whipped at a high speed as it cools. The oils must be well below their melting point in order to properly entrap air during whipping to achieve a desired and stable consistency.

Lavender Essential Oil

Lavender essential oil (lavender oil) is extracted from the Lavender plant (*Lavandula angustifolia*). Lavender Essential Oil is also commonly known as English Lavender, Garden Lavender, Common Lavender, True Lavender, and Narrow-Leaved Lavender. It is medium-strength floral, herbaceous, sweet, and woody aroma presents a top-middle fragrance note. The oil is well-known for its relaxing effects on the body. Therapeutic-grade lavender is highly regarded for the skin. It may be used to cleanse cuts, bruises and skin irritations.

Typically, lavender essential oil is extracted by steam distillation. This process utilizes steam to extract oil from the lavender buds. The steam then carries that oil to a flask where the liquid and oil separate.

Lavender essential oil has been used as an anxiolytic drug, a mood stabilizer, a sedative, a spasmolytic, an antihypertensive, antimicrobial, an analgesic agent and as a wound healing accelerator, as well as oil inhalation for the treatment of migraine.

Lemon Grass Essential Oil

Lemongrass is a tropical herb with a strong citrus flavor. In the garden, lemongrass forms a tall, grassy clump 3 to 5 feet tall. Lemongrass has a long history of use in culinary preparation especially in Asian cuisines Due to its appealing scent Lemongrass essential oil (lemongrass oil) is often used in aromatherapy. Inhaling the scent of the oil (or using the oil in carrier oils, body oils, and hair and skin products) is said to offer a variety of benefits.

One of the main components of lemongrass essential oil is citral, a compound found to act as an antimicrobial (a substance that destroys or suppresses the growth of microorganisms, including bacteria and fungi). Lemongrass essential oil also contains limonene, a compound shown to reduce inflammation and possess antibacterial properties.

A study published in the Journal of Alternative and Complementary Medicine suggests that brief exposure may possess anti-anxiety properties. Participants in the study inhaled lemongrass oil or one of two control substances. Immediately after the inhalation, each study participant was stressed with a color and word test. Those who inhaled the lemongrass essential oil had a reduction in anxiety and tension and were quicker to recover from the anxiety than those who took the tea tree oil.

Tangerine Essential Oil

Tangerine essential oil has a high level of the monoterpene limonene that is known for its ability to have stimulating and enhancing effects on mood. Limonene in tangerine essential oil is also known for its cleansing and purifying properties. Tangerine essential oil is an excellent source of antioxidants, gives relief from spasms by inducing relaxation in the organ systems, improves circulation, and supports a healthy immune system The chemical composition of tangerine essential oil includes, but is not limited to: alpha-pinene, alpha-thujone, beta-pinene, camphene, citronellol, gamma terpinolene, geranial, limonene, linalool, myrcene, nerol, sabinene, and terpineol.

Arnica Oil and Butter

The genus *Arnica* comprises approximately 40 species. *A. montana* is the most well-known species. *Arnica* is an herbaceous perennial in the daisy family (Asteraceae) with leaves that form a basal rosette from which emerges a one- to two-foot stalk with orange-yellow flowers. Though the flowers are the primary parts used medicinally, the dark brown, cylindrical rhizomes are also have medicinal use.

*Arnica montana* is endemic to Europe, where it is relatively widespread, growing wild from Norway to the Balkans and from Spain to Ukraine. There is some commercial cultivation occurring mainly in Germany, France, Italy, Switzerland, and Chile. Additional common names for *A. montana* include European *arnica*, leopard's bane, wolf's bane and mountain tobacco. There are species native to North America, *A. fulgens*, *A. sororia*, and *A. cordifolia*, which can be use interchangeably with *A. Montana* for the purpose of this invention.

*Arnica* tinctures (hydroalcoholic extracts) and salves have been used externally for their anti-inflammatory, bactericidal, antineuralgic, antirheumatic, antiseptic, counterirritant, and wound-healing effects. *Arnica* preparations are also used topically to treat boils, bruises, contusions, edema, hematoma, insect bites, joint pain (including rheumatic conditions), sprains, phlebitis, thrombosis, muscle pain, and sudden hair loss It is advised to use *Arinca* topically on unbroken skin. It should be noted that *arnica* contains chemical constituents, notably helenalin and its derivatives, that are allergenic and may cause topical dermatitis in some individuals.

*Arnica* is used commercially in cosmetics, shampoos, hair tonics, anti-dandruff products, and bath products, and *arnica* oil is used in perfumery. Both *Arnica* butter and *Arnica* oil are suitable for use with the present invention.

White Beeswax

Beeswax (*cera alba*) is a natural wax produced by honey bees of the genus *Apis*. The wax is formed into scales by eight wax-producing glands in the abdominal segments of worker bees, which discard it in or at the hive. The hive workers collect and use it to form cells for honey storage and larval and pupal protection within the beehive. Chemically, beeswax consists mainly of esters of fatty acids and various long-chain alcohols.

Bees wax is frequently used in pharmaceutical and cosmetic preparations. A study in Journal der Deutschen Dermatologischen Gesellschaft found beeswax to be superior to similar barrier creams—compared to mineral oil-based creams, such as petroleum jelly—when used according to its protocol.

Beeswax works is used cosmetic products because of the wax esters that exist in both beeswax and human skin. It is these compounds which help to bind and emulsify ointments, lipsticks and lotions. Beeswax is a natural hydrating composition that increases essential moisture in the skin.

White beeswax is the wax separated from the honeycomb of the hive bee. The wax is then bleached by exposing it in thin layers to the action of the air, sunlight, and moisture. The process may also be accelerated by the aid of chemicals, such as potassium bichromate and sulphuric acid. This process results in a nearly white, translucent mass. Its specific gravity ranges between 0.958 to 0.970 or about 0.950 to 0.960 at 25° C. White beewax has a melting point of about 61° to about 64°.

Common Ingredients

The following are other common ingredients used in the invention. These common ingredients are often used in mixtures, lotions, cosmetics and tinctures. These are readily recognizable to one of skill in the art: Apricot Kernel Oil, Avacado Butter, Avocado oil, Camphor, *Capsicum*, Carrot Butter, Cinnamon bark oil, Dill seed oil, *Eucalyptus* oil, Frankincense oil, Hemp seed oil, Menthol, Pumpkin Butter, Tomato flower oil, Tomato leaf oil, Vitamin E.

Lotions, Creams, Mixtures and Tinctures of the Invention

The above ingredients can be combined to contain a therapeutic amount of CBD combined with the other ingredients to suit the need of the practitioner. Below are Examples of embodiments of the invention. The disclosure of which ought to teach one of skill in the art to make and use the invention according to their needs.

EXAMPLES

The examples below are not meant to be limiting. The examples are disclosed to show the most effective embodiments of the invention for use in the inventors study, with the parameters of available test subjects. These examples are presented as exemplars, to illustrate the use of the invention and convey its properties so that one skilled in the art and modifies the inventions for their particular needs and situation.

Example 1

Massage Oil

A therapeutic massage oil containing, inter alia, CBD has been be created according to the following instructions using the ingredients described above and specifically listed below:

| Group 1 | | |
|---|---|---|
| Sweet Almond oil | 384 oz | 73% |
| Avocado oil | 40 oz | 8% |
| Apricot Kernel Oil | 40 oz | 8% |
| Hemp seed oil | 40 oz | 8% |

| Group 2 | | |
|---|---|---|
| Lavender oil | 1 oz | 0.015% |
| Tangerine Oil | 1 oz | 0.015% |
| Lemongrass Oil | 1 oz | 0.015% |
| Frankincense Oil | 1 oz | 0.015% |
| Eucalyptus Oil | 1 oz | 0.015% |
| Vitamin E Oil | 1 oz. | 0.015% |
| Arnica Oil | 4 oz | 1% |
| CBD | 4.2 oz | ~1% |

The massage oil was prepared starting with the almond oil in a sufficiently large pot. The pot and oil are heated up to 100 F under continuous stirring, slowly brought to 100 F in about 10 to 20 minutes. When the oil reached 100 F, the Avocado oil, Apricot Kernel Oil, Hemp seed oil and vitamin E oil were added and stirred. The mixture of oils remained under heat for about two hours with continuous stirring until 190 F is reached. At this temperature, the Lavender oil, Tangerine Oil, Lemongrass Oil, Frankincense Oil, *Eucalyptus* Oil, Vitamin E Oil, *Arnica* Oil and CBD oil were added. Heating was sustained at 190 F for 20 minutes while being stirred continuously. After twenty minutes the heat was reduced and the mixture was allowed to cool slowly while still stirring continuously. Cooling was controlled to allow of a gradual cooling back to 100 F in about 4 hours. While still warm (100 F) the lotion was bottled in small aliquots for use or sale.

Example 2

Pain Relief Cream

A pain relief cream containing, inter alia, CBD has been be created according to the following instructions using the ingredients described above and specifically listed below:

| Group 1 | | |
|---|---|---|
| Body Butter | 128 oz | 27% |
| White bees wax | 48 oz | 10% |
| Shea butter | 64 oz | 13.5% |
| Coco Butter | 78 oz | 17% |
| Coconut oil | 48 oz | 10% |
| Arnica Butter | 32 oz | 7% |
| Aloe | 48 oz | 10% |
| Arnica Oil | 8 oz | 2% |
| Vitamin E | 4 oz | 1% |

| Group 2 | | |
|---|---|---|
| Lavender oil | 12 ml or ½ oz | <.1% |
| Lemongrass oil | 20 ml or 2/3 oz | <.1% |
| Tangerine oil | 60 ml or 2 oz | ½% |
| CBD | 232 ml or 8 oz | 2% |

Body butter, White Bees wax, Shea butter, cocoa butter, Coconut oil, *arnica* butter, aloe, *arnica* oil and Vitamin E oil we combined in a large pot/double boiler.

The mixture was heated to 190 degrees F. with constant stirring. At this temperature, Lavender oil, Tangerine Oil, Lemongrass Oil, Frankincense Oil, Tangerine Oil and CBD oil were added. Heating was sustained at 190 F for 20 minutes while continuing to stir. After twenty minutes the heat was reduced and the mixture was allowed to cool slowly while maintaining agitation.

At 164 degree F., the combination was transferred to a suitably sized mixing apparatus with a whip mixer attachment. Whipping air was incorporated into the batch until it has cooled to less than 80 degrees F. but more than 72 degrees F. The lotion was transferred to jars to finish cooling and stored before sale and use.

The lids were left off until cream was cooled to room temperature to avoid condensation (approx. 8 hours). Afterward, the lids were installed.

Example 3

Gardeners Relief Cream

A therapeutic Gardeners Relief Cream containing, inter alia, CBD has been created according to the following instructions using the ingredients described above and specifically listed below:

| Group 1 | | |
|---|---|---|
| Body butter | 120 oz | 25% |
| White bees wax | 48 oz | 10% |
| Carrot Butter | 80 oz | 17% |
| Pumpkin Butter | 64 oz | 13.5% |
| Avocado Butter | 64 oz | 13.5% |
| Aloe 1x | 56 oz | 12% |
| Arnica butter | 32 oz | 7% |
| Arnica oil | 4 oz | ¾% |
| Vitamin E | 4 oz | ¾% |

| Group 2 | | |
|---|---|---|
| Dill seed oil | 10 ml | <.2% |
| Tomato flower oil | 25 ml | <.2% |
| Tomato leaf oil | 1 drop | <.1% |
| Lavender oil | 20 ml | <.2% |
| Frankincense oil | 5 ml | <.1% |

-continued

| Group 2 | | |
|---|---|---|
| Eucalyptus oil | 5 ml | <.1% |
| CBD | 240 ml or 8 oz | 2% |
| TOTAL | 474 oz | |

The gardener relief oil was prepared starting with adding the body butter to a sufficiently large pot. The pot and oil were heated up to 100 F under continuous stirring, slowly being brought to 100 F in about 10 to 20 minutes. When the oil reached 100 F, white bees wax, carrot butter, pumpkin butter, avocado butter, aloe, *arnica* butter, *arnica* oil and vitamin E oil were added and stirred. The mixture remained under heat for about two hours with continuous stirring until 190 F was achieved. At this temperature, the dill seed oil, tomato flower oil, tomato leaf oil, lavender oil, frankincense oil, *eucalyptus* oil and CBD oil were added. Heating was sustained at 190 F for 20 minutes while stirring continuously. After twenty minutes the heat was reduced and the mixture was allowed to cool slowly while stirring continuously. Cooling was controlled to allow for a gradual cooling back to 100 F in about 4 hours. While still warm (100 F) the lotion was bottled in small aliquots for use or sale.

Example 4

Warming Cream

A therapeutic warming Cream containing, inter alia, CBD has been created according to the following instructions using the ingredients described above and specifically listed below:

| Group 1 | | |
|---|---|---|
| Body butter | 80 oz | 26% |
| White bees wax | 30 oz | 10% |
| Shea butter | 30 oz | 10% |
| Coco butter | 50 oz | 16% |
| Coconut oil (92° F.) | 30 oz | 10% |
| Arnica butter | 20 oz | 7% |
| Aloe 1x | 30 oz | 10% |
| Arnica oil | 5 oz | 2% |
| Vit E | 2.5 oz | 1% |

| Group 2 | | |
|---|---|---|
| Eucalyptus oil | 20 ml< | .1% |
| Frankincense oil | 20 ml< | .1% |
| Camphor | 50 ml< | .2% |
| Capsicum | 30 ml< | .1% |
| Cinnamon bark oil | 25 ml< | .1% |
| Menthol | 600 ml dry 20 oz | 7% |
| CBD | 150 ml 5 oz | 2% |

The warming cream was prepared to start with the body butter in a sufficiently large pot. The pot and oil were heated up to 100 F under continuous stirring, slowly brought to 100 F in about 10 to 20 minutes. When the oil reached 100 F, white bees wax, shea butter, cocoa butter, coconut oil, *arnica* butter, aloe 1×, *arnica* oil, and Vitamin E, were added and stirred. The mixture remained under heat for about two hours with continuous stirring until 190 F was reached. At this temperature, *eucalyptus* oil, frankincense oil, camphor, *capsicum*, cinnamon bark oil, menthol and CBD oil were added. Heating was sustained at 190 F for 20 minutes while continuing to stir. After twenty minutes the heat was reduced and the mixture was allowed to cool slowly while stirring continuously. Cooling was controlled to allow for a gradual cooling back to 100 F in about 4 hours. During cooling, the mixture was stirred at a relatively high speed to prevent separation. While still warm (100 F) the lotion was bottled in small aliquots for use or sale.

Example 5

Hand and Body Lotion Grip

A Hand and Body Lotion Grip containing, inter alia, CBD has been created according to the following instructions using the ingredients described above and specifically listed below:

| Group 1 | | |
|---|---|---|
| Lotion Base | 800 oz | 78% |
| Shea butter | 50 oz | 5% |
| Coconut oil | 92 degrees 50 oz | 5% |
| Arnica Butter | 25 oz | 2.5% |
| Arnica oil | 12.5 oz | 1.25% |
| Aloe 1x | 50 oz | 5% |
| Vit E | 12.5 oz | 1.25% |
| Hemp oil | 6 oz | .6% |

| Group 2 | | |
|---|---|---|
| Lavender oil | 38 ml or 1.25 oz | <.1% |
| Tangerine oil | 100 ml or 3.3 oz | <.3% |
| Lemongrass oil | 50 ml or 1.7 oz | <.15% |
| CBD | 250 ml or 8.3 oz | .8% |

The Hand and Body Lotion Grip was prepared to start with the lotion base, shea butter, coconut oil, *arnica* butter, *arnica* oil, aloe, vitamin E and hemp oil mixed together in a sufficiently large pot. The pot and mixture were heated up to 100 F under continuous stirring, slowly brought to 170 F in about 10 to 20 minutes. The mixture remained at 170 F for 10-20 minutes. Stirring is recommended to prevent scorching. When it was confirmed that all the ingredients were combined into a consistent mixture, lavender oil, tangerine oil, lemongrass oil, and CBD oil were added. After adding the second group of ingredients, heating was sustained at 170 F for 20 minutes while continuing to stir. After twenty minutes the heat was reduced and the mixture is allowed to cool slowly while stirring continuously. Cooling was controlled to allow for a gradual cooling back to 100 F in about 4 hours. While still warm (75 F) the lotion was bottled in small aliquots for use or sale. It is noted that the batch can be bottled when the temperature is below 75 F. However, to avoid condensation, if the batch is above room temperature do not seal the bottle. The product was cooled completely to room temperature before sealing the bottles.

Example 6

Massage Lotion Glide

A massage lotion glide containing, inter alia, CBD has been created according to the following instructions using the ingredients described above and specifically listed below:

| Group 1 | | |
| --- | --- | --- |
| Lotion Base | 800 oz | 79% |
| Shea Butter | 50 oz | 5% |
| Coconut oil | 92 degrees 50 oz | 5% |
| Arnica Butter | 25 oz | 2.5% |
| Arnica oil | 12.5 oz | 1.25% |
| Vitamin E | 12.5 oz | 1.25% |
| Hemp oil | 50 oz | 5% |

| Group 2 | | |
| --- | --- | --- |
| Lavender | 37.5 mls or 1.25 oz | <.1% |
| Tangerine oil | 100 mls or 3.3 oz | <.3 |
| Lemongrass oil | 50 mls or 1.6 oz | <.1% |
| CBD | 250 mls or 8.3 oz | <.8% |

The Massage Lotion Glide was prepared to start with the lotion base, shea butter, coconut oil, arnica butter, arnica oil, vitamin E and hemp oil mixed together in a sufficiently large pot. The pot and mixture were heated up to 100 F under continuous stirring, slowly brought to 170 F in about 10 to 20 minutes. The mixture remained at 170 F for 10-20 minutes. Stirring was required, and recommended, to prevent scorching. When it was confirmed that all the ingredients have combined into a consistent mixture, lavender, tangerine oil, lemongrass oil and CBD oil were added. After adding the second group of ingredients, heating was sustained at 170 F for 20 minutes while continuing to stir. After twenty minutes the heat was reduced and the mixture was allowed to cool slowly while stirring continues. Cooling was controlled to allow of a gradual cooling back to 100 F in about 4 hours. While still warm (75 F) the lotion was bottled in small aliquots for use or sale. The batch can be bottled when the temperature is below 75 F. However, to avoid condensation, if the batch is above room temperature do not seal the bottle. Let the product cool completely to room temperature before sealing the bottles. This example was allowed to cool to room temperature prior to capping.

Example 7

Gardeners Relief Lotion

A therapeutic Gardeners Relief Lotion containing, inter alia, CBD has been created according to the following instructions using the ingredients described above and specifically listed below:

| Group 1 | | |
| --- | --- | --- |
| Lotion Base | 800 oz | 73% |
| Pumpkin Butter | 50 oz | 5% |
| Avocado Butter | 50 oz | 5% |

-continued

| Group 1 | | |
| --- | --- | --- |
| Carrot Butter | 25 oz | 2.5% |
| Arnica Butter | 25 oz | 2.5% |
| Aloe 1x | 100 oz | 9% |
| Arnica oil | 13 oz | 1.25% |
| Vitamin E | 13 oz | 1.25% |

| Group 2 | | |
| --- | --- | --- |
| Lavender oil | 30 mls or 1 oz | <.1% |
| Dill Seed oil | 38 mls or 1.25 oz | <.1% |
| Tomato Flower | 65 mls or 2 oz | <.2% |
| Tomato leaf oil | 10 ml or .3 oz | <.1% |
| Frankincense oil | 10 ml or .3 oz | <.1% |
| Eucalyptus oil | 10 ml or .3 oz | <.1% |
| CBD | 300 mls or 10 oz | .9% |

The Gardeners Relief Lotion was prepared to start with the lotion base, pumpkin butter, avocado butter, carrot butter, arnica butter, aloe 1x, arnica oil and Vitamin E mixed together in a sufficiently large pot. The pot and mixture were heated up to 100 F under continuous stirring, slowly brought to 170 F in about 10 to 20 minutes. The mixture remained at 170 F for 10-20 minutes. Stirring was required, and recommended, to prevent scorching. When it was confirmed that all the ingredients have combined into a consistent mixture, lavender oil, dill seed oil, tomato flower, tomato leaf oil, frankincense oil, eucalyptus oil and CBD oil were added. After adding the second group of ingredients, heating was sustained at 170 F for 20 minutes while continuing to stir. After twenty minutes the heat is reduced and the mixture is allowed to cool slowly while stirring continuously. Cooling was controlled to allow for a gradual cooling back to 100 F in about 4 hours. While still warm (75 F) the lotion was bottled in small aliquots for use or sale. The batch can be bottled when the temperature is below 75 F. To avoid condensation, if the batch is above room temperature do not seal the bottles. Let product cool completely to room temperature before sealing the bottles. This example was allowed to cool to room temperature prior to capping.

We claim:

1. A sealed bottle or a sealed jar consisting essentially of sweet almond oil, cannabidiol oil, aloe vera, lavender, white bees wax, shea butter, hemp seed oil, coconut oil, lemongrass, and arnica butter.

* * * * *